(12) United States Patent
Kim et al.

(10) Patent No.: US 6,565,355 B2
(45) Date of Patent: May 20, 2003

(54) APPARATUS FOR PRECISELY LOCATING AN ORTHODONTIC BRACKET AT A PREDETERMINED POSITION ON A SURFACE OF A TOOTH

(75) Inventors: Tae Weon Kim, Seoul (KR); Gi Sun Bae, Pusan (KR); Jae Hyung Cho, Seoul (KR)

(73) Assignee: Invisi-Tech Co., Ltd., Seoul (KR)

( * ) Notice: Subject to any disclaimer, the term of this patent is extended or adjusted under 35 U.S.C. 154(b) by 0 days.

(21) Appl. No.: 09/896,842

(22) Filed: Jun. 29, 2001

(65) Prior Publication Data

US 2003/0003415 A1 Jan. 2, 2003

(30) Foreign Application Priority Data

Aug. 25, 2000 (KR) .................................... 2000-0049591

(51) Int. Cl.[7] ................................................ A61C 3/00
(52) U.S. Cl. ........................................................ 433/3
(58) Field of Search ............................. 433/3, 8, 9, 24

(56) References Cited

U.S. PATENT DOCUMENTS

| | | | |
|---|---|---|---|
| 3,521,355 A | * | 7/1970 | Pearlman |
| 3,738,005 A | * | 6/1973 | Cohen et al. |
| 3,871,098 A | * | 3/1975 | Dean |
| 4,014,096 A | * | 3/1977 | Dellinger |
| 4,134,208 A | * | 1/1979 | Pearlman |
| 4,183,141 A | * | 1/1980 | Dellinger et al. |
| 4,523,908 A | * | 6/1985 | Drisaldi et al. |
| 4,626,208 A | * | 12/1986 | Hall ................................ 433/3 |
| 5,055,038 A | * | 10/1991 | Ronay et al. ................... 433/24 |
| 5,055,039 A | * | 10/1991 | Abbatte et al. ................ 433/24 |
| 5,304,061 A | * | 4/1994 | Nelson ............................. 433/8 |
| 5,542,842 A | * | 8/1996 | Andreiko et al. ............... 433/3 |
| 5,711,665 A | | 1/1998 | Adam et al. |
| 5,863,198 A | * | 1/1999 | Doyle ............................. 433/3 |
| 5,879,156 A | | 3/1999 | Deleo |
| 6,123,544 A | | 9/2000 | Cleary |
| 6,290,495 B1 | | 9/2001 | Jabri |

* cited by examiner

Primary Examiner—Ralph A. Lewis
(74) Attorney, Agent, or Firm—Akerman Senterfitt

(57) ABSTRACT

In an apparatus for precisely locating an orthodontic bracket at a predetermined position on a surface of a tooth, orthodontic brackets for holding orthodontic wires can be easily and precisely located at and adhered to a predetermined position on a surface of a tooth, not only at an initial time but also even when the used orthodontic brackets are separated from the surface of the tooth in the course of the orthodontic treatment. The apparatus has a suspension body, a ring, and a molding spacer. The suspension body is disposed extending in parallel with the tooth from an apex toward a dental root of the tooth with a predetermined gap. The ring is inserted in the groove and hooked around the hook after the holding member has been fittedly inserted in the fitting recess, to thereby tightly assemble the suspension body and the orthodontic bracket together. The molding spacer is disposed between the suspension body and the tooth.

17 Claims, 14 Drawing Sheets

APPARATUS FOR PRECISELY LOCATING AN ORTHODONTIC BRACKET AT A PREDETERMINED POSITION ON A SURFACE OF A TOOTH

BACKGROUND OF THE INVENTION

1. Field of the Invention

The present invention relates to an apparatus for precisely locating and adhering an orthodontic bracket, and more particularly to an apparatus for precisely locating an orthodontic bracket at a predetermined position on a surface of a tooth, in which orthodontic brackets for holding orthodontic wires can be easily and precisely located at and adhered to a predetermined position on a surface of a tooth, not only at an initial time but also even when the used orthodontic brackets are separated from the surface of the tooth in the course of the orthodontic treatment.

2. Description of the Related Art

In general, one's teeth are an important factor in presenting his or her external features, since their color and shape have a large effect on the image formed by the external appearance. Also, it has been known that one's teeth are an important factor in forming one's external image, since the set of teeth according to the arrangement of teeth has an effect on not only the teeth themselves but also the skeletal structure of the face. Especially, in the case of a person who has malformed set of teeth, his or her teeth not only may have an effect on his or her external appearance but also may cause inconvenience to his or her dietary life. Therefore, the correction of irregular set of teeth, or the orthodontic correction of teeth, has been considered as an important subject of medical treatment in dentistry.

Under such circumstances as above, the orthodontics of the dental treatments has a long history, and the method or the technique of the orthodontics has been remarkably developed. In a conventional orthodontics, which has been widely performed until recent times, orthodontic brackets are adhered to the set or teeth, which are to be corrected, one bracket by one tooth, and then holding members respectively formed at the brackets are tied together by an orthodontic wire made from a material having a large strength, so that the irregular set of teeth is gradually corrected for a long time by the tension force of the orthodontic wire.

However, in the conventional method as described above, since the orthodontic brackets of a predetermined size are adhered to the external side surfaces, or the labial-side surfaces, of teeth, the brackets and the orthodontic wire ligating the brackets are exposed to others' eyes during the daily life of the patient who has to be placed under the orthodontic treatment, which causes a trouble in the patient's appearance.

In order to overcome this problem in the external appearance, proposed has been another orthodontic treatment, which has recently been going popular, and in which the orthodontic brackets are adhered to the inner side surfaces, or the lingual side surfaces, of the teeth, and then the brackets are tied together by an orthodontic wire, so that the orthodontics is performed by the tension force of the orthodontic wire. Although the patients to be placed under the orthodontic treatment greatly prefer this orthodontic treatment since the structures for the orthodontic treatment are hidden by the patient's teeth, the doctors performing the orthodontics have much difficulty in the labors of handling the orthodontic brackets and of ligating the holding members of the brackets by the orthodontic wire. Therefore, there has been anticipated an improvement capable of settling such difficulty as above.

In detailed description, the orthodontic brackets for correcting the irregular set of teeth can be adhered to at least six teeth including the front tooth and the canine tooth at each of the upper and the lower jaws. After the orthodontic brackets are firstly adhered one by one to each of the teeth, and then the holding members of the orthodontic brackets have to be tied together by a much thinner iron wire in order to ligate the holding members of the orthodontic brackets by means of the orthodontic wire made from the material having a large strength. In this case, since this labor of tying the holding members together by the thin iron wire has to be delicately carried out, careful attention and endeavor are required for each tooth and it takes relatively long time in performing the above labor and the orthodontic treatment, which inevitably causes inconvenience and difficulty to both the dentist and the patient.

A Korean Patent Application entitled "Automatic lingual side ligated orthodontic bracket for correcting an irregular set of teeth" was filed by the present applicants on the same date as the priority date of the present application. The Korean Patent Application discloses a one-touch type lingual side ligated orthodontic bracket for correcting an irregular set of teeth, which includes a base having an adhesion surface to be adhered to the lingual side surface of each tooth and a holding member for holding an orthodontic wire. In the bracket, when a handle disposed at a body of the holding member is pushed, a cover is automatically opened, so that the orthodontic wire restrained by the cover can be separated therefrom. When the apparatus of the present invention is used in combination with this one-touch type lingual side ligated orthodontic bracket for correcting an irregular set of teeth, the efficiency of the labor of correcting an irregular set of teeth can be maximized.

In fact, according to the orthodontic technique in the dentistry, an original model for a patient's set of teeth is firstly made by means of a mold, and an ideal model after treating and correcting the patient's set of teeth is made on the base of the original model. Thereafter, various elements for the correction into the ideal state of the set of teeth, including adhered locations of the orthodontic brackets on the surfaces of the teeth, an arrangement of the orthodontic wire, etc., are determined, and then the real orthodontics is performed. In other words, the orthodontic brackets are made on the basis of the teeth model, and then they are applied to the patient's corresponding teeth.

Further, in order to adhere the orthodontic brackets to the labial side surfaces or the lingual side surfaces of the teeth for correcting irregularities of teeth, most desired positions for seating the orthodontic brackets have to be determined and then the orthodontic brackets have to be exactly adhered onto the positions. However, these labors are by no means easy, require a careful endeavor, and are relatively time-exhaustive. Moreover, when one orthodontic bracket or several orthodontic brackets are separated from the surfaces of the teeth while the orthodontic treatment is in progress, much further endeavor and attention are required in adhering them to the original positions.

In the orthodontic treatment, to locate the orthodontic brackets at exact positions on the surfaces of teeth is an important factor in order to obtain a successful result of treatment. Especially, in the case of the lingual side orthodontic treatment, in which the exact location of the orthodontic brackets has a large influence on the treatment, usually used is an indirect bonding method, in which the orthodontic brackets are adhered to ideal positions on well-arranged teeth model and then the positions of the orthodontic brackets are exactly transferred to the patient's teeth, rather than a direct bonding method, in which the orthodontic brackets are directly adhered to the surfaces of the teeth.

Among the existing apparatuses used in the indirect bonding method, when a material of silicon or rubber is used, it is difficult to exactly locate the orthodontic brackets due to the elasticity of the material. When a solid resin is used, the positions of the orthodontic brackets can be exactly transferred, but it is impossible to adhere the orthodontic brackets again when the orthodontic brackets have been separated from the surfaces of the teeth once used. Further, although it is possible to manufacture an apparatus capable of re-adhering the orthodontic brackets simultaneously while using the resin, there are several problems in this apparatus, in that the orthodontic brackets may be separated from the apparatus for adhesion while the bonding is carried out and it is difficult to adhere the orthodontic brackets again to the exact positions once separated, since the apparatus for adhesion and the orthodontic brackets are assembled together only by means of a frictional force.

Therefore, there has been a request for a method or an apparatus of guiding the orthodontic brackets to be rapidly and easily located at precise positions, when the orthodontic brackets are initially adhered to the surfaces of teeth requiring the orthodontic correction, and when the separated orthodontic brackets are adhered again.

SUMMARY OF THE INVENTION

Accordingly, the present invention has been made in an effort to solve the problems occurring in the related art, and it is an object of the present invention to provide an apparatus for precisely locating an orthodontic bracket at a predetermined position on a surface of a tooth, in which orthodontic brackets for holding orthodontic wires can be easily and precisely located at and adhered to a predetermined position on a surface of a tooth.

It is another object of the present invention to provide an apparatus for precisely locating an orthodontic bracket at a predetermined position on a surface of a tooth, in which orthodontic brackets for holding orthodontic wires can be easily and precisely located at and adhered to a predetermined position on a surface of a tooth, not only at an initial time but also even when the used orthodontic brackets are separated from the surface of the tooth in the course of the orthodontic treatment.

In accordance with one aspect, the present invention provides an apparatus for precisely locating an orthodontic bracket at a predetermined position on a surface of a tooth, the apparatus comprising a suspension body, a ring, and a molding spacer. In this case, the orthodontic bracket includes a base member having an adhesion surface to be adhered to the surface of the tooth, and a holding member and a hook respectively integrated with the base member, the holding member holding an orthodontic wire to be ligated by the orthodontic wire for correcting irregular set of teeth.

The suspension body is disposed extending in parallel with the tooth from an apex toward a dental root of the tooth with a predetermined gap. Preferably, the suspension body has an inner surface, at a lower end of which a fitting recess is formed, and an outer surface, on a lower portion of which a groove is formed, the fitting recess having a concave contour complementary to a contour of the holding member, so that the holding member can be fittedly inserted in the fitting recess.

The ring is inserted in the groove and hooked around the hook after the holding member has been fittedly inserted in the fitting recess, to thereby tightly assemble the suspension body and the orthodontic bracket together.

The molding spacer is disposed between the suspension body and the tooth, which has first and second surfaces respectively facing the tooth and the suspension molding. It is preferred that the first surface has a concave contour complementary to a contour of the upper area of the tooth, which includes an apex and upper portions of a labial surface and a lingual surface of the tooth, so that the molding spacer can be fittedly placed on the upper area of the tooth. Also, the second surface may have a contour complementary to a concave contour of the inner surface of the suspension body, so that the suspension body can be fittedly placed on the molding spacer.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF PREFERRED EMBODIMENTS

The above and other objects, characteristics, and advantages of the present invention will be apparent from the following description along with the accompanying drawings.

Figure 1A:
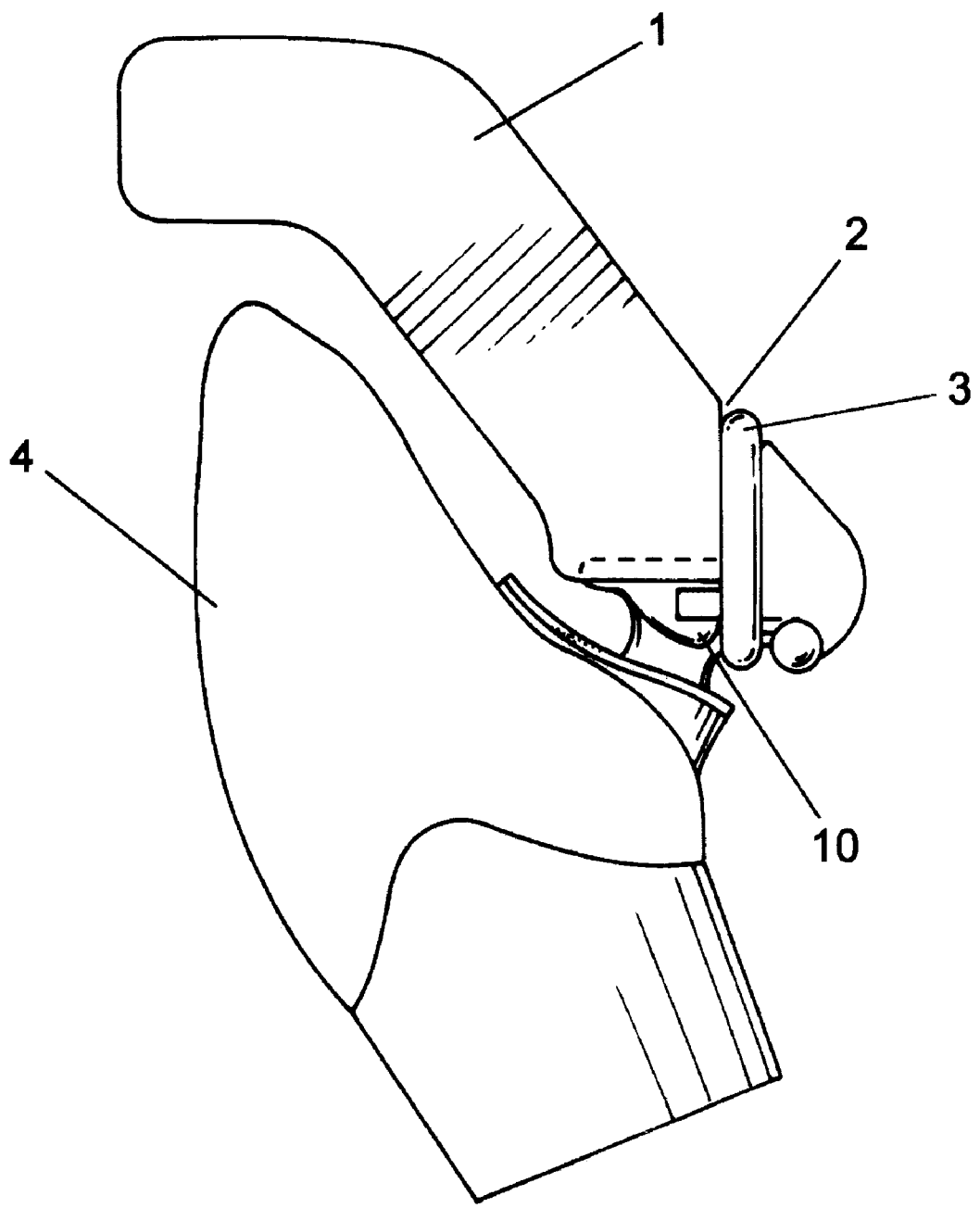
FIGS. 1A and 1B are side views of an apparatus for precisely locating an orthodontic bracket at a predetermined position on a surface of a tooth according to an embodiment of the present invention, respectively when the orthodontic bracket is located at the predetermined position and when a suspension body is separated after the orthodontic bracket is located.
Figure 1B:
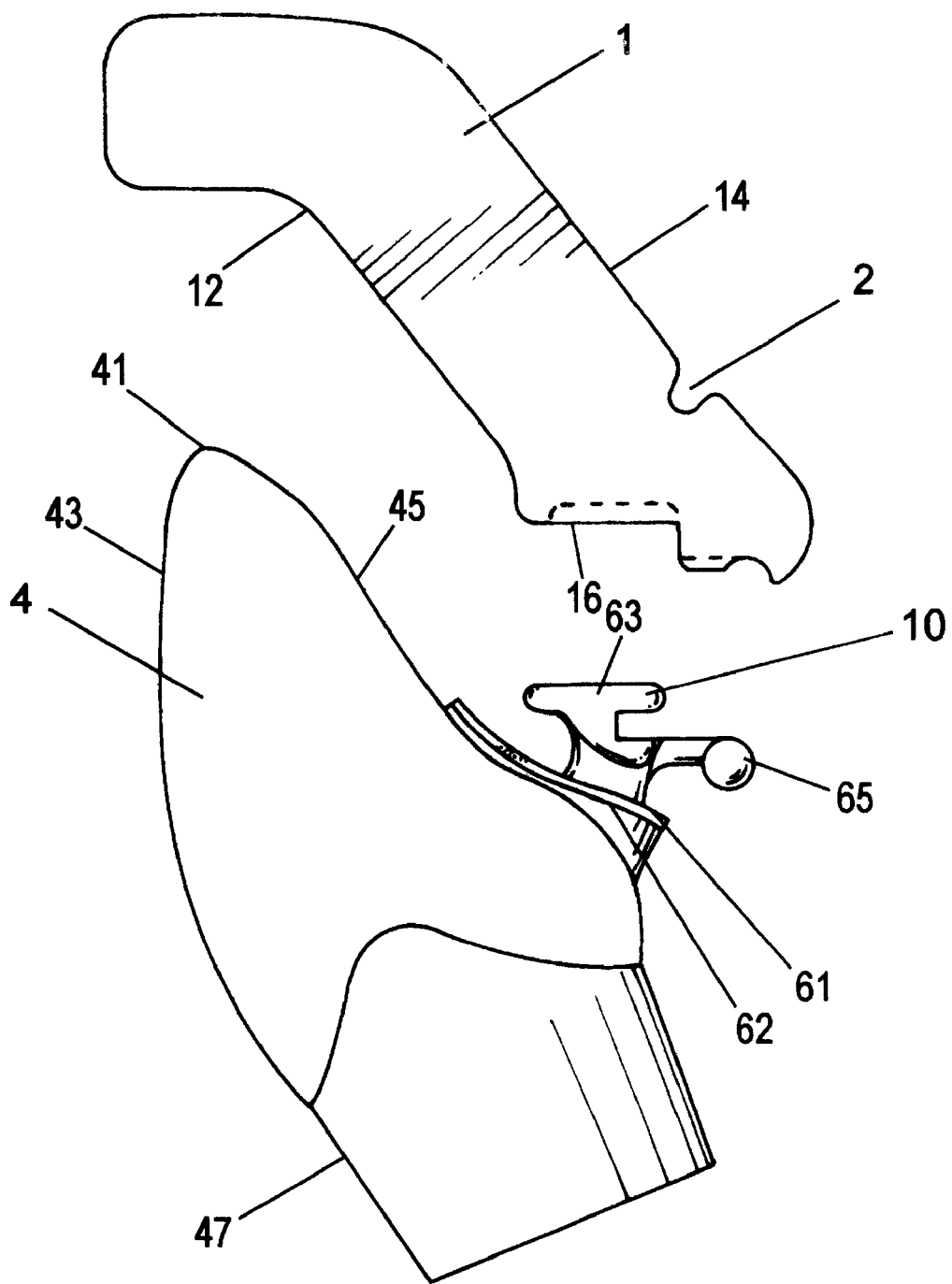

According to a preferred embodiment of the present invention, provided is an apparatus for precisely locating an orthodontic bracket at a predetermined position on a surface of a tooth. The apparatus of the invention includes a suspension body 1, a ring 3, and a molding spacer 5. In this case, the orthodontic bracket 10 is a ligated bracket for an orthodontic correction of teeth, which includes a base member 61 having an adhesion surface 62 to be adhered to a surface of the tooth, and a holding member 63 and a hook 65, which are integrated with the base member 61 and respectively protrude upward and inward of an oral cavity as shown in FIGS. 1A and 1B. The holding member 63 is a member to hold and to be ligated by an orthodontic wire (not shown) for correcting irregular set of teeth.

In the meantime, the suspension body 1 of the apparatus according to the invention is disposed extending in parallel with a tooth 4 from an apex 41 toward a dental root 47 of the tooth 4 with a predetermined gap. Further, the suspension body 1 has an inner surface 12, at a lower end of which is formed an fitting recess 16, and an outer surface 14, on a lower portion of which is formed a groove 2. In this case, the fitting recess 16 has a concave contour complementary to the contour of the holding member 63, so that the holding member 63 can be fittedly inserted in the fitting recess 16.

The ring 3 is made from an elastic material and functions to tighten the suspension body 1 and the orthodontic bracket 10 together. That is, when the holding member 63 has been fittedly inserted in the fitting recess 16, the ring 3 is inserted in the groove 2 and hooked around the hook 65, so as to tightly assemble the suspension body 1 and the orthodontic bracket 10 together.

Figure 3:
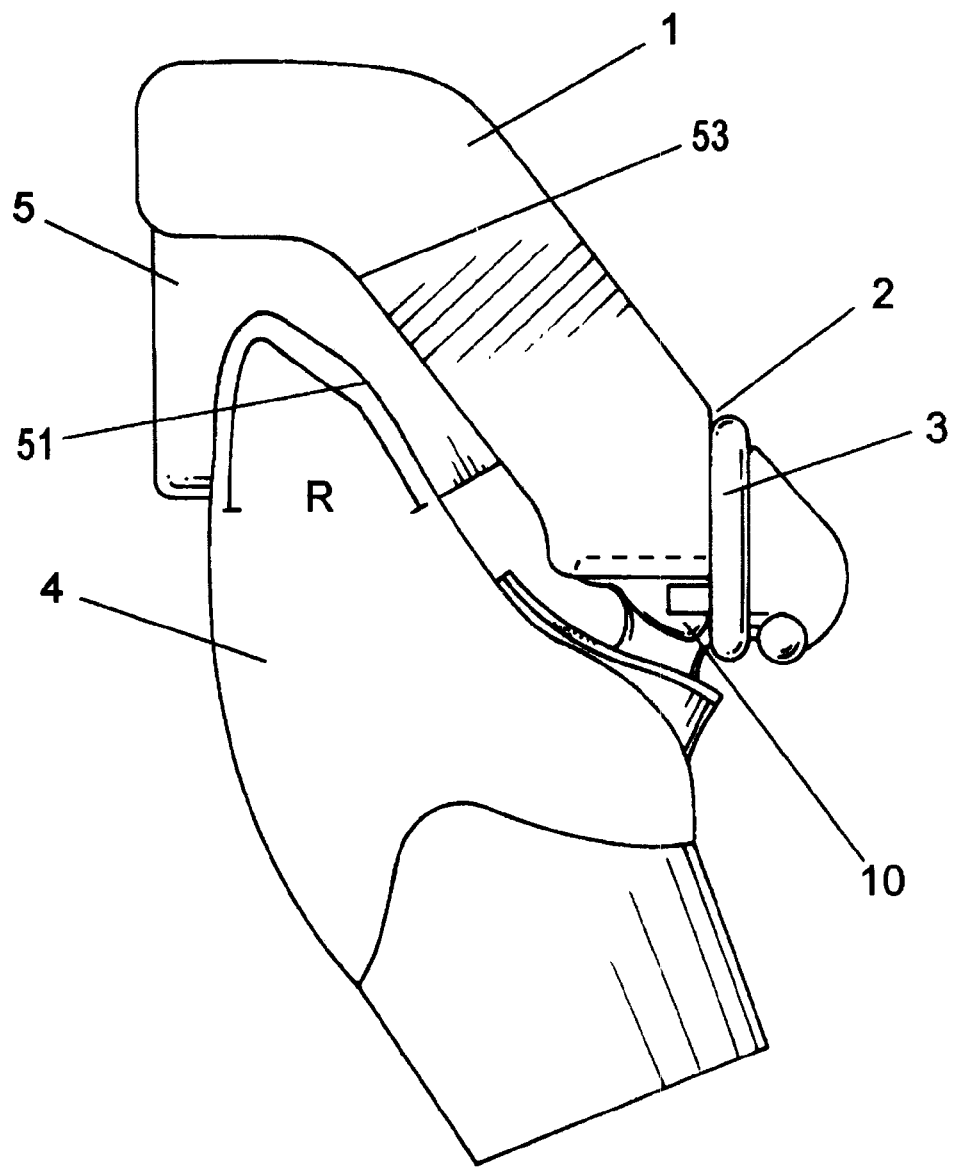
FIG. 3 is a side view of the apparatus shown in FIGS. 1A and 1B in an assembled state, in which a molding spacer is disposed between a suspension body and a tooth, so as to ensure the orthodontic bracket to be located at the predetermined position.

The molding spacer 5 is disposed between the suspension body 1 and the tooth 4. The molding spacer 5 has first and second surfaces 51 and 53. The first surface 51 has a concave contour complementary to the contour of the region R, which includes an apex 41 and upper portions of a labial surface 43 and a lingual surface 45 of the tooth 4 as shown in FIG. 3, so that the molding spacer 5 can be fittedly placed on the top of the tooth 4. Also, the second surface 53 has a contour complementary to a concave contour of the inner surface 12 of the suspension body 1, so that the suspension body 1 can be fittedly placed on the molding spacer 5. Therefore, when the molding spacer 5 has been fittedly placed on the top of the tooth 4 and the suspension body 1 has been fittedly placed on the molding spacer 5, the molding spacer 5 can provide a stable support for the suspension body 1 without a detail movement of the suspension body 1, to thereby enable the suspension body 1 to precisely locate the orthodontic bracket 10 at a predetermined position on the lingual surface 45 of the tooth 4.

It is preferred that the molding spacer 5 is made from synthetic resin, that the elastic ring 3 is made from rubber, and that the orthodontic bracket 10 is a lingual side orthodontic bracket for the teeth of upper and lower jaws.

In the apparatus of the present invention, since there is provided the molding spacer 5 having a concave contour complementary to the contour of the corresponding tooth, even when the orthodontic bracket 10 is separated from the surface of the tooth due to such a cause as a poor adhesion during the orthodontic treatment, it can be placed again at the original position without any difficulty. Therefore, it is preferred that the apparatus of the invention is separately stored, since it is necessary not only for adhering the orthodontic bracket when the orthodontic treatment is initiated but also for re-adhering the orthodontic bracket when it is separated in the course of the treatment.

The apparatus of the invention is an apparatus for an indirect boning, made from resin or plastic, so as to precisely transfer the relation between the tooth and the orthodontic bracket. In this indirect bonding apparatus, since the orthodontic bracket is tightly assembled with the apparatus by mean of a rubber ring or an assembling pin, the orthodontic bracket can be easily detached and assembled again. It is apparent that this assembling method may be applied to not only the lingual side orthodontic bracket as described above but also a general labial side orthodontic bracket or tube.

Hereinafter, the function and working effect by the apparatus of the invention will be described, with reference to the accompanying drawings.

Firstly, a molding spacer 5 having a concave contour complementary to that of a tooth in question and a suspension body 1 having a size capable of locating the orthodontic bracket 10 at a desired position on the tooth are arranged.

Then, as shown in FIGS. 1A and 1B, the holding member 63 is fittedly inserted in the fitting recess 16, and then the ring 3 is inserted in the groove 2 and hooked around the hook 65, so that the orthodontic bracket 10 is tightly assembled with the suspension body 1. In this case, since the fitting recess 16 has a concave contour complementary to the contour of the holding member 63, the suspension body 1 and the orthodontic bracket 10 are fittedly assembled without a minute relative movement.

The lingual surface 45 of the tooth 4, to which the orthodontic bracket 10 is to be adhered, is prepared for bonding as usual. If desired for additional bond strength, the adhesion surface 62 of the base member 61 can be sand-blasted. Then, an adhesive is applied to the adhesion surface 62 of the orthodontic bracket 10.

Thereafter, the molding spacer 5 is fittedly placed on the area R of the molding spacer 5, and the suspension body 1 is fittedly placed on the molding spacer 5, so that the orthodontic bracket 10 is precisely located at the predetermined position on the orthodontic bracket 10. Then, the orthodontic bracket 10 is pressed onto the lingual surface 45, and excessive bonding material is removed before the adhesive sets. After the adhesive has set, the suspension body 1 and the molding spacer 5 are removed. The removed the suspension body 1 and the molding spacer 5 are stored for the case where they are necessary.

Figure 2A:
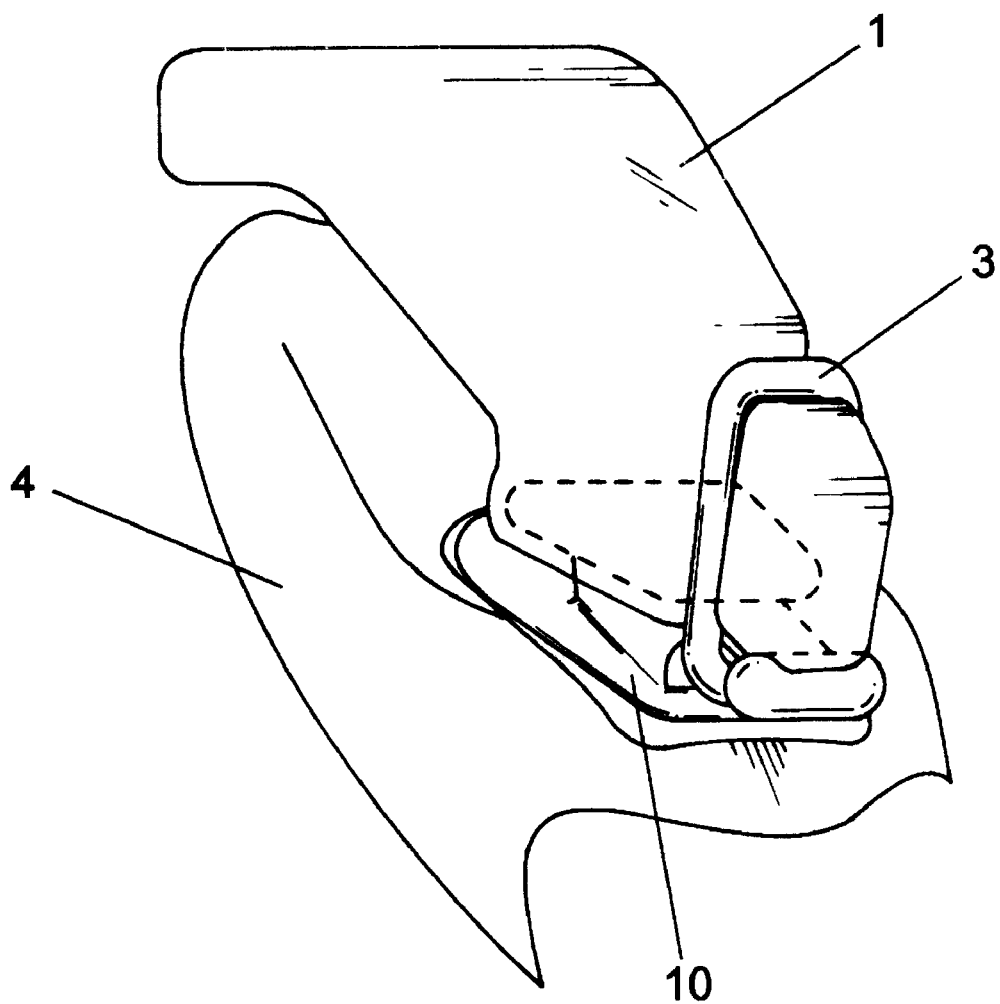
FIGS. 2A and 2B are perspective views for describing the states shown in FIGS. 1A and 1B.
Figure 2B:
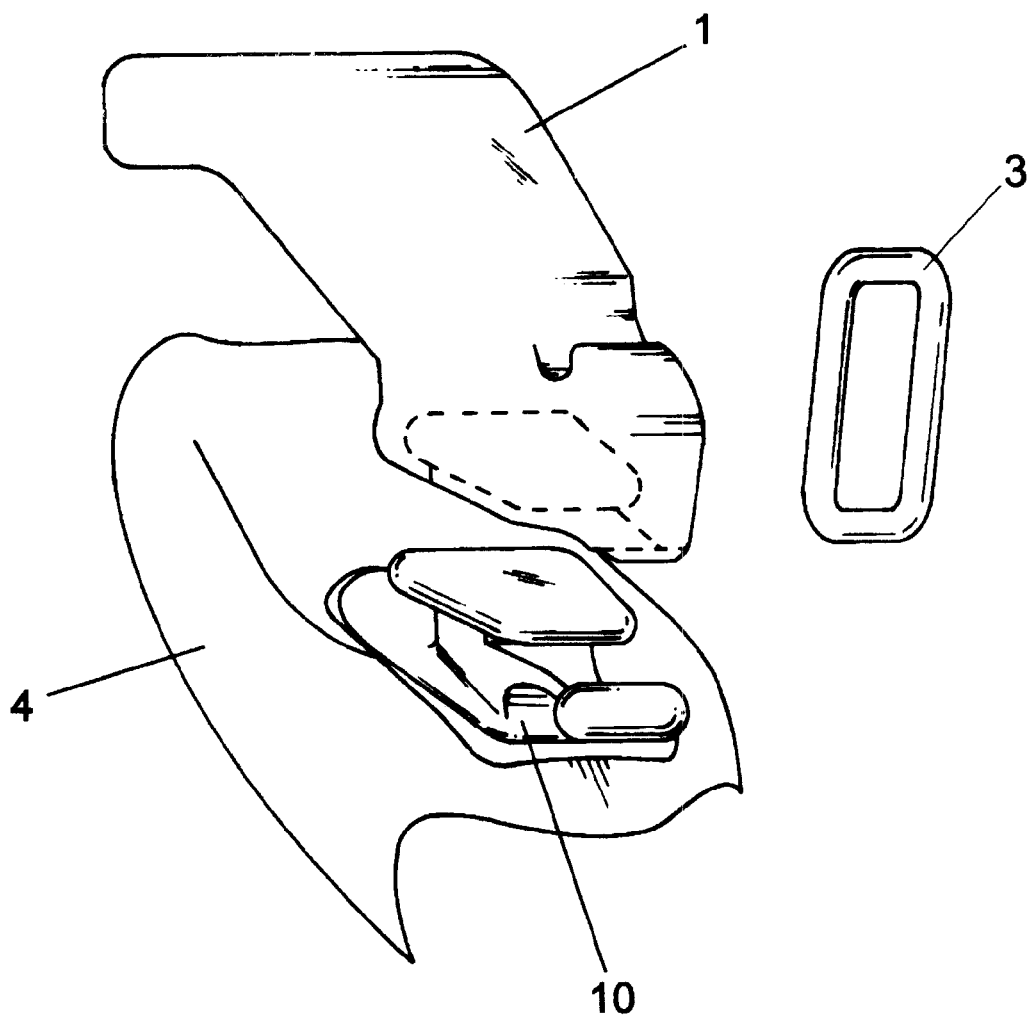

As shown in FIGS. 2A and 2B, the inner surface 12 of the suspension body 1 is spaced apart from the lingual surface 45 of the tooth 4 with a predetermined gap, into which the auto-polymerizing resin is filled to transfer the contour of the tooth. In this case, there is arranged a small interval between the tooth side portion and the bracket side portion, through which excessive adhesive leaking when the adhesion surface 62 is adhered to the lingual surface 45 can be drained instead of being introduced toward the lingual surface 45 of the tooth 4. FIG 3. shows an assembled state of the apparatus of the invention.

Figure 4A:
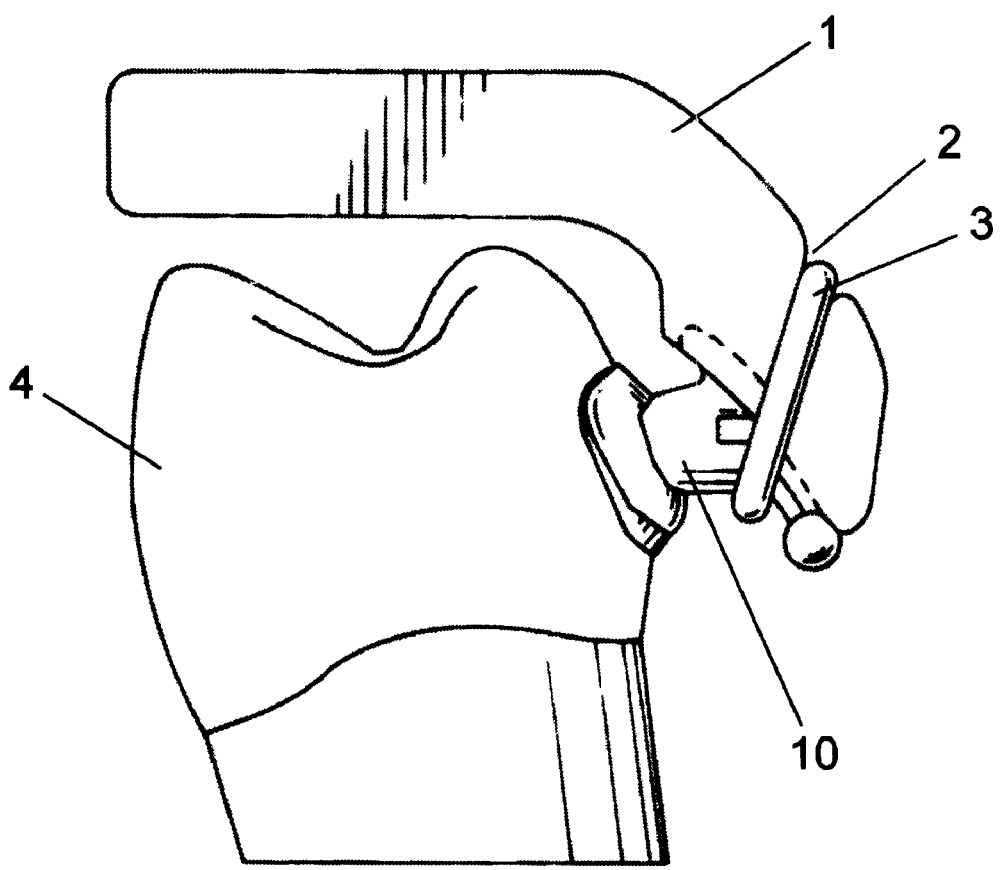
FIGS. 4A and 4B are side views for showing an apparatus according to another embodiment of the present invention, which is used for an orthodontic bracket for a premolar tooth of an upper jaw or a lower jaw.
Figure 4B:
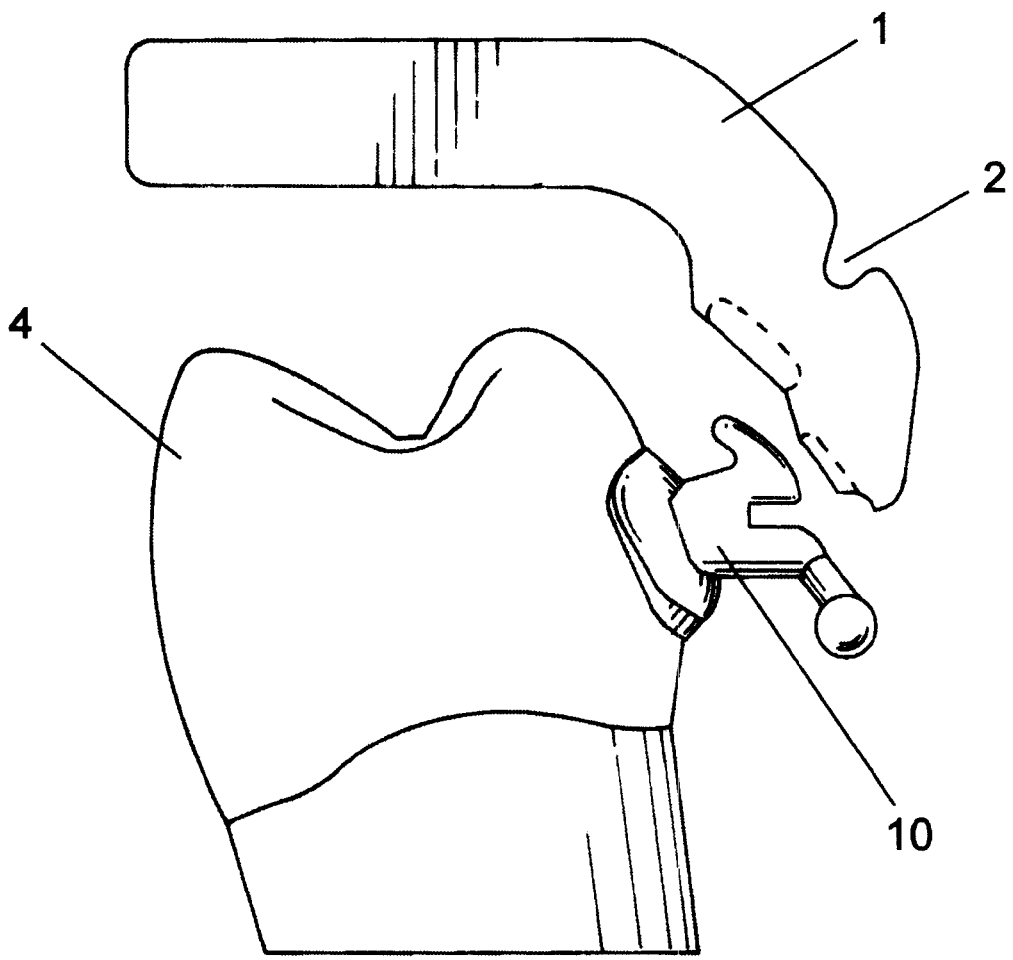
Figure 5A:
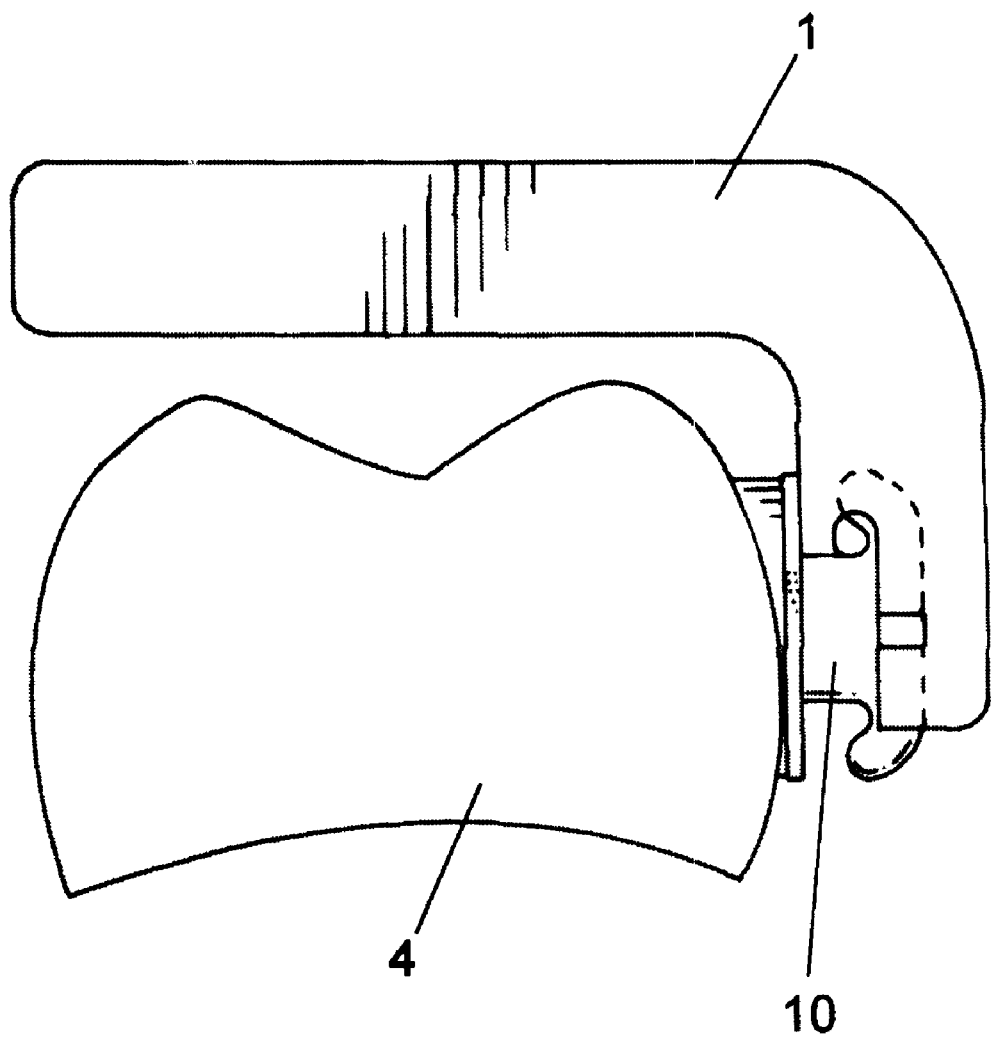
FIGS. 5A and 5B are side views of an apparatus for precisely locating an orthodontic bracket according to another embodiment of the present invention, respectively when the orthodontic bracket is located at the predetermined position and when a suspension body is separated after the orthodontic bracket is located.
Figure 5B:
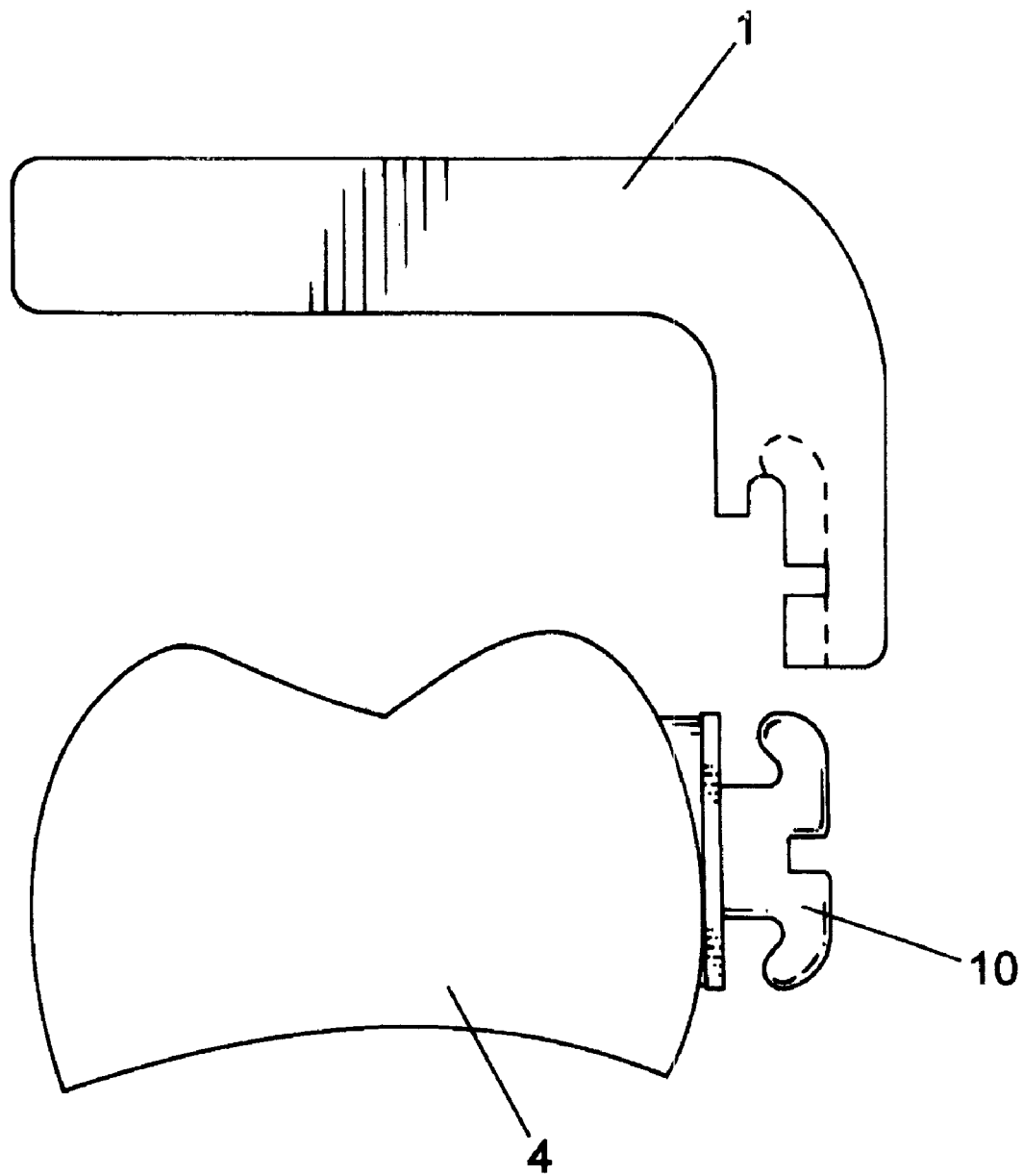
Figure 6A:
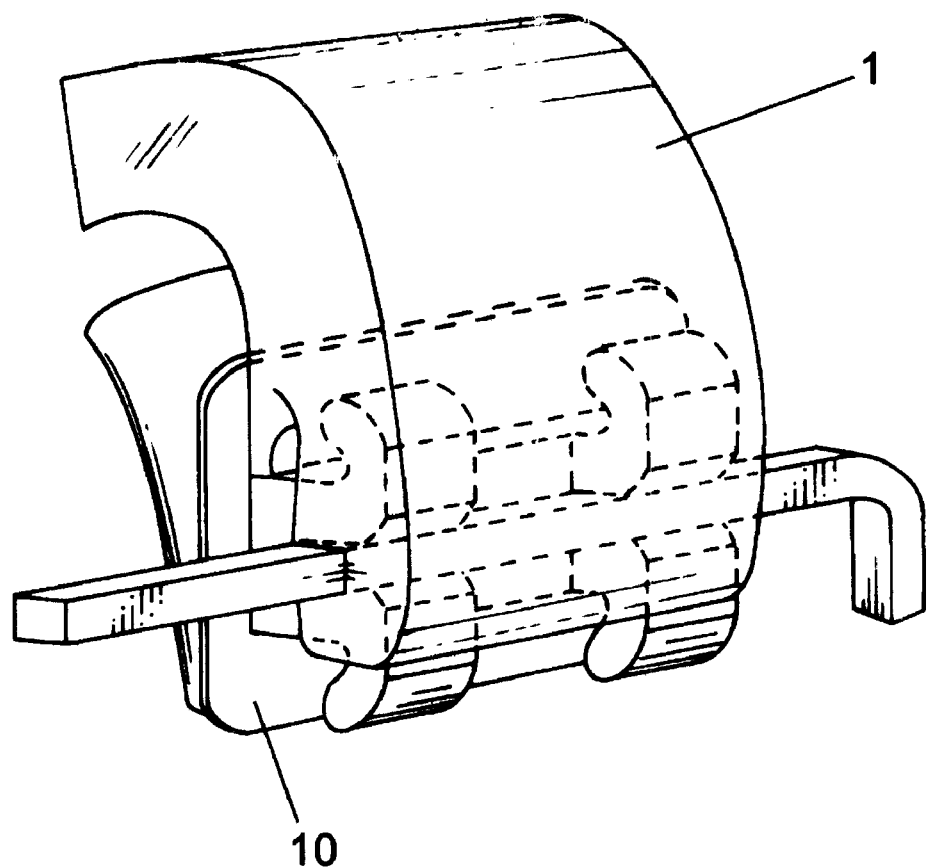
FIGS. 6A and 6B are side views for showing the construction of an apparatus according to another embodiment of the present invention.
Figure 6B:
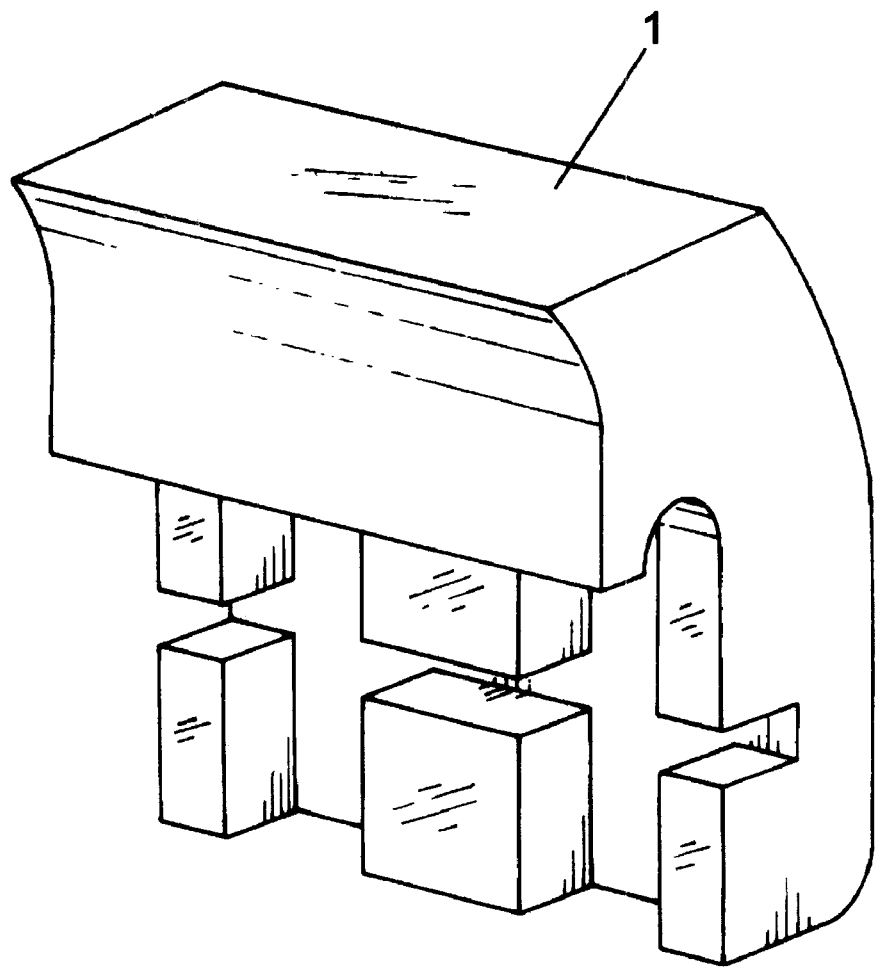

FIGS. 4A and 4B show an apparatus according to another embodiment of the present invention, which is used for an orthodontic bracket for a premolar tooth of an upper jaw or a lower jaw, manufactured by Ormco/"A" Company, located at 1717 W. Collins, Orange, Calif. 82867, U.S.A. Although the basic construction of this apparatus is similar to that of an apparatus for the front teeth, the concave contour of the fitting recess and the position of the groove change according to the shape of the used orthodontic bracket.

FIGS. 5A to 6B show an apparatus according to another embodiment of the present invention, which is used for a labial orthodontic bracket, and in which the labial orthodontic bracket is assembled with the suspension body by means of an assembling pin instead of the rubber ring. The thickness of the pin changes according to the size of the slot of the used orthodontic bracket.

In this apparatus, the orthodontic bracket 10 does not have the hook 65 but has the holding member 63 extending in a shape of letter Y, and the fitting recess 16 of the suspension body 1 has a concave contour complementary to the shape of the holding member 63 and slots formed both sides thereof, through which a pin can be inserted. After the holding member 63 is inserted in the fitting recess 16, the pin is inserted through the slots to stably and firmly assemble the suspension body 1 and the orthodontic bracket 10 together. When the pin is drawn out, the suspension body 1 and the orthodontic bracket 10 can be easily and simply separated from each other.

This construction can be employed also in an orthodontic tube, which can be assembled with a suspension body by a pin inserted through slots. Likewise, when the pin is drawn out, the orthodontic tube and the suspension body can be easily separated from each other.

Figure 7A:
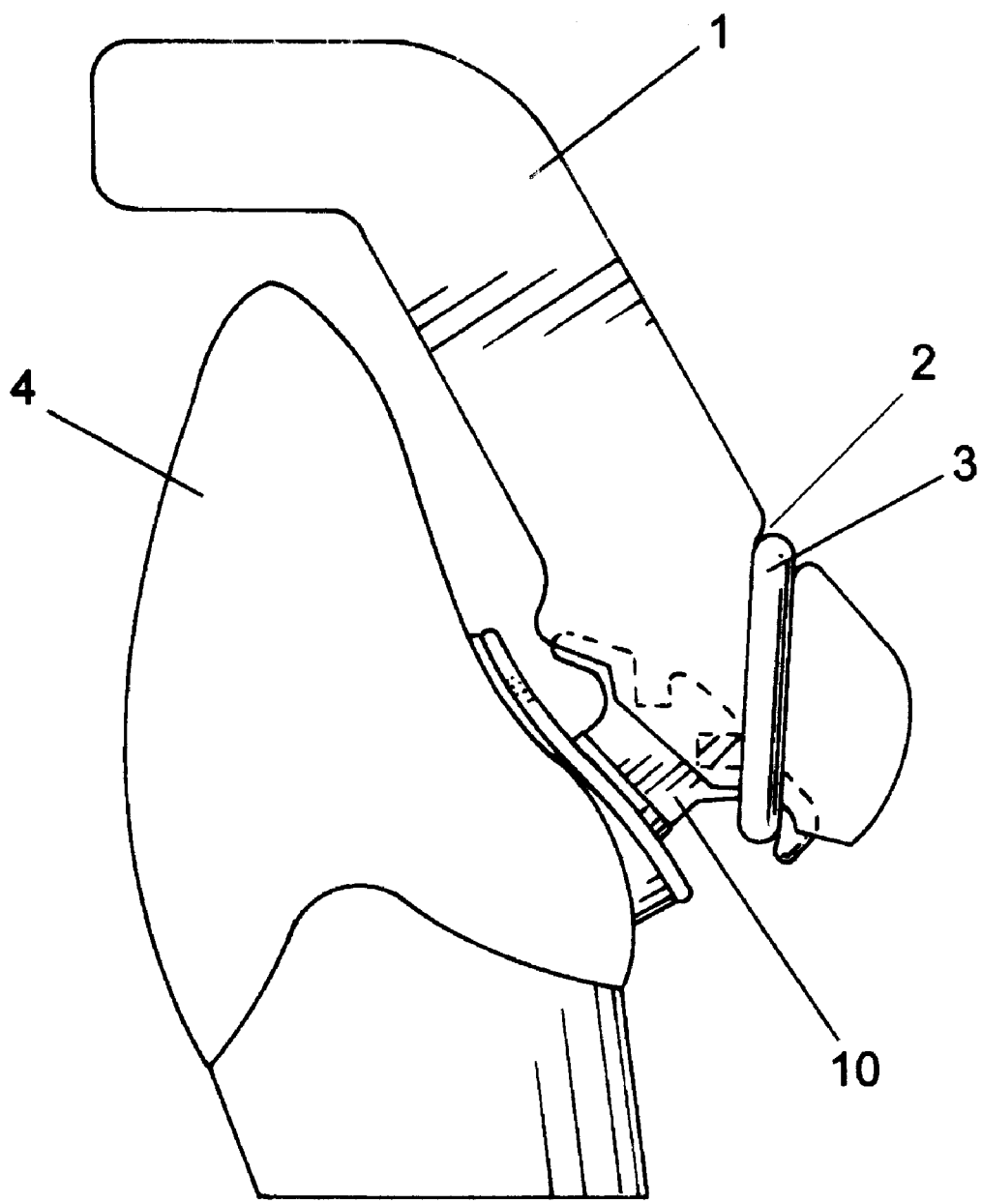
FIGS. 7A and 7B are side views for showing an apparatus for indirect bonding according to another embodiment of the present invention, respectively when the orthodontic bracket is located at the predetermined position and when a suspension body is separated after the orthodontic bracket is located.
Figure 7B:
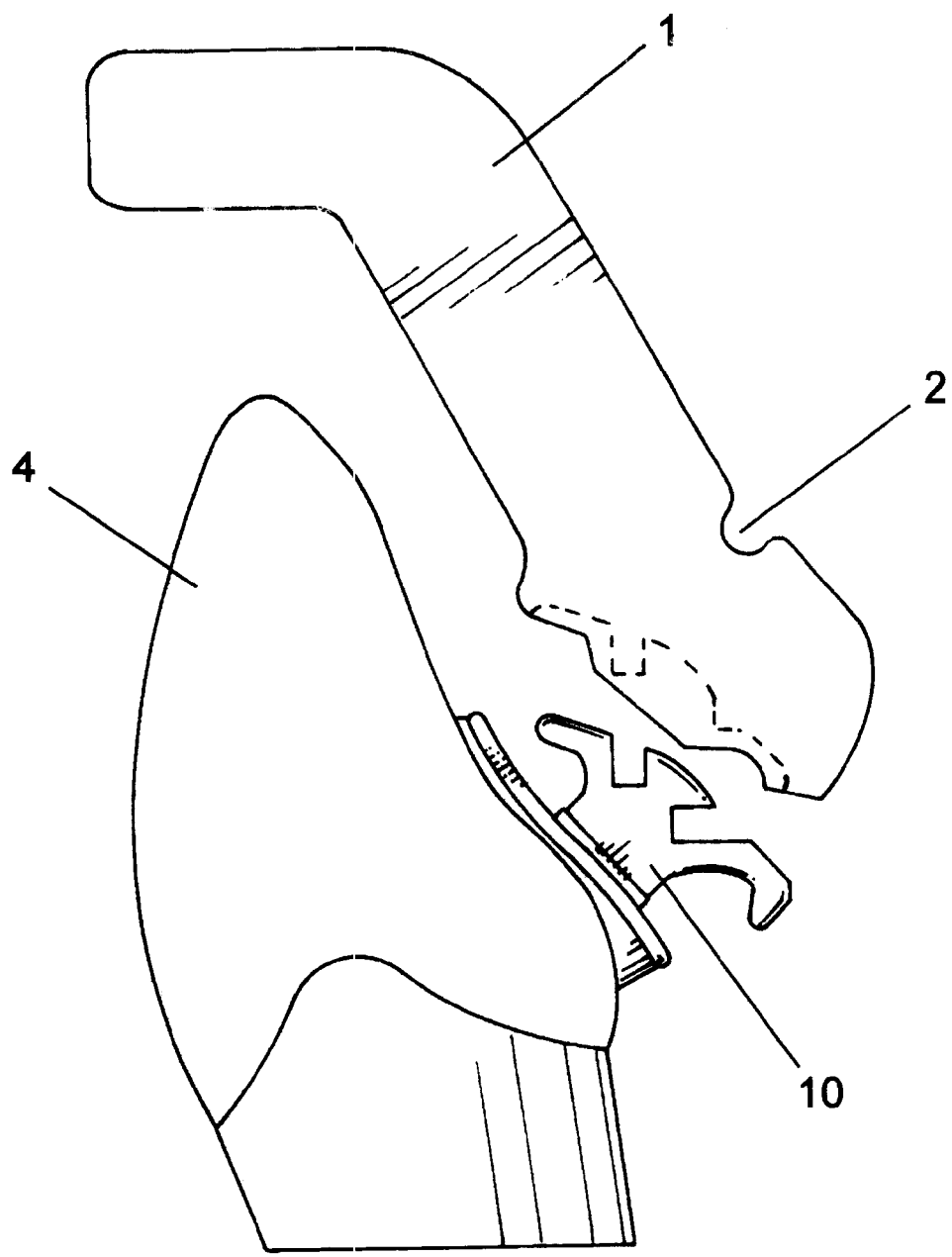
Figure 8:
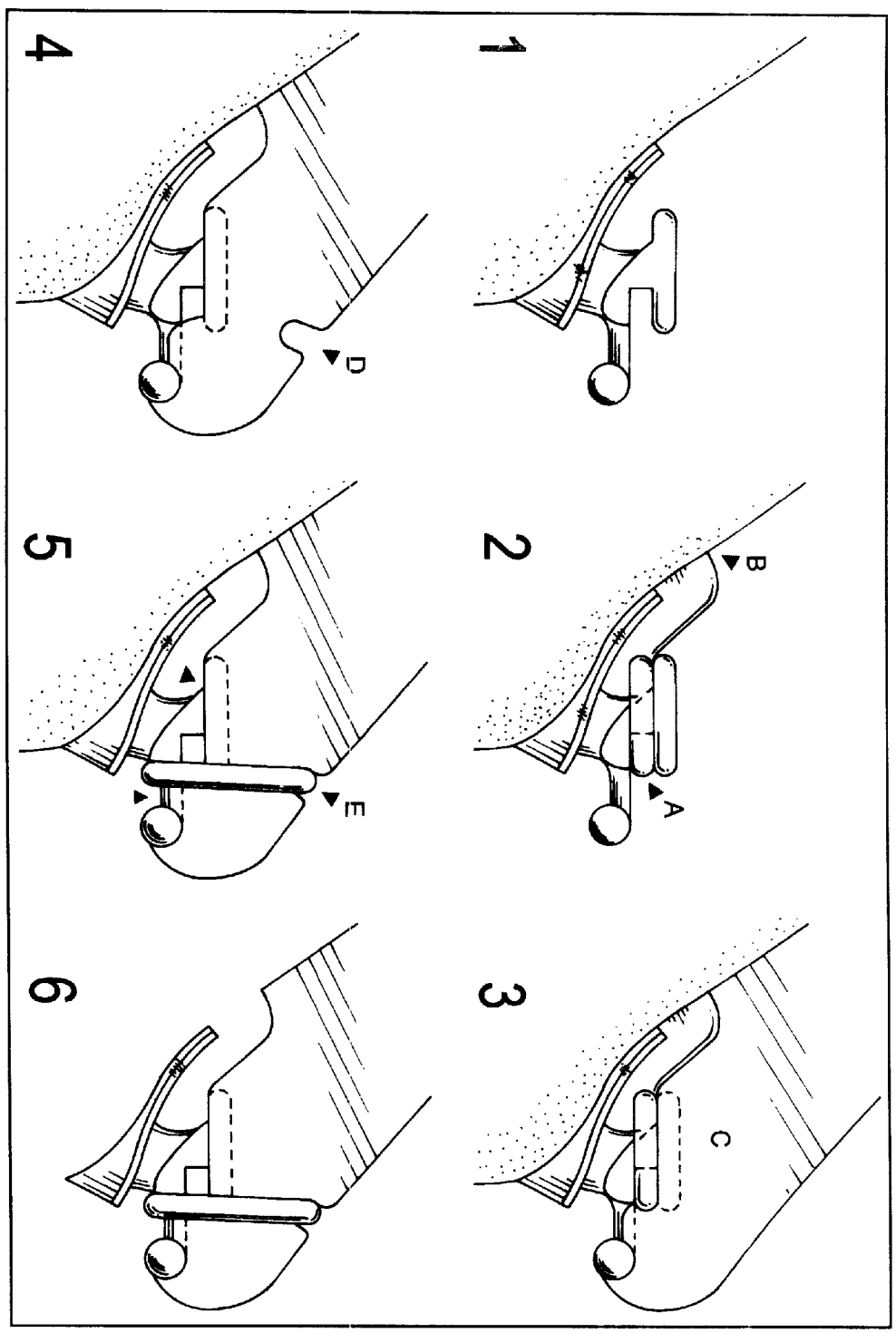
FIG. 8 is a view for sequentially showing a process of locating and adhering an orthodontic bracket at a predetermined position on a surface of a tooth by an apparatus of the present invention.

FIGS. 7A and 7B show an apparatus for indirect bonding according to another embodiment of the present invention, which is used for Huzida's lingual orthodontic bracket, which is similar to the Ormco's apparatus for indirect bonding for front teeth orthodontic bracket but a concave contour complementary to Huzida's orthodontic bracket and a groove for an O-ring.

The apparatus of the invention may be used together with the automatic lingual side ligated orthodontic bracket, which was filed in the Korean Patent Property Office (KIPO) on the same date as the priority date of the present application. In this case, the orthodontic treatment can have a multiplied effect.

In an apparatus for precisely locating an orthodontic bracket at a predetermined position on a surface of a tooth according to the present invention as described above, orthodontic brackets for holding orthodontic wires can be easily and precisely located at and adhered to a predetermined position on a surface of a tooth, not only at an initial time but also even when the used orthodontic brackets are separated from the surface of the tooth in the course of the orthodontic treatment.

Therefore, the apparatus of the invention largely reduces the dentist's endeavor and the patient's inconveniences, and moreover provides a renovating momentum in the technique of orthodontics or orthodontic treatment in dentistry.

While there have been illustrated and described what are considered to be preferred specific embodiments of the present invention, it will be understood by those skilled in the art that the present invention is not limited to the specific embodiments thereof, and various changes and modifications and equivalents may be substituted for elements thereof without departing from the true scope of the present invention.

What is claimed is:

1. An apparatus for transferring an orthodontic bracket to a precisely predetermined position on a surface of a tooth, said apparatus comprising:
   a first means for suspending the orthodontic bracket, wherein said first means is configured for engaging a holding member of the orthodontic bracket that is to be ligated;
   a second means for securing the orthodontic bracket with said first means, said orthodontic bracket being capable of being separated from said first means by said second means; and
   a third means adapted for fitted placement on an upper area of the tooth and for stably supporting said first means so as to enable the orthodontic bracket assembled with said first means to be precisely located at the predetermined position on the surface of the tooth.

2. An apparatus as claimed in claim 1, wherein said first means, said second means, and said third means are adapted for assembling with the orthodontic bracket having a base member with an adhesion surface to be adhered to the surface of the tooth, and a holding member integrated with the base member, the holding member holding an orthodontic wire to be ligated by the orthodontic wire for correcting irregular set of teeth.

3. An apparatus as claimed in claim 2, wherein said first means comprises a suspension body having a fitting recess, for fitted engagement with the holding member of the orthodontic bracket so as to enable the orthodontic bracket and said suspension body to be stably assembled together by said second means.

4. An apparatus as claimed in claim 3, wherein said filling recess has a concave contour complementary to a contour of the holding member for fitted insertment of the holding member in said fitting recess.

5. An apparatus as claimed in claim 3, wherein said suspension body is adapted to extend in parallel with the tooth from an apex toward a dental root of the tooth with a predetermined gap.

6. An apparatus as claimed in claim 3, wherein said second means comprises a pin inserted through side walls of said fitting recess, and the holding member of the orthodontic bracket is fixed by said pin after being inserted in said fitting recess.

7. An apparatus as claimed in claim 3, wherein said suspension body has an inner surface, at a lower end of which said fining recess is formed, and an outer surface, on a lower portion of which a groove is formed.

8. An apparatus as claimed in claim 7, wherein said third means comprises a molding spacer disposed between said suspension body and the tooth, wherein said molding spacer has first and second surfaces respectively facing the tooth and said suspension molding.

9. An apparatus as claimed in claim 8, wherein said first surface of said molding spacer has a contour complementary to a contour of the upper area of the tooth, said contour of said first surface for fitted placement of said molding spacer on the upper area of the tooth, which includes an apex and upper portions of a labial surface and a lingual surface of the tooth.

10. An apparatus as claimed in claim 8, wherein said second surface of said molding spacer has a contour complementary to a contour of said inner surface of said suspension body, said contour of said second surface for fitted engagement of said molding spacer with said suspension body.

11. An apparatus as claimed in claim 8, wherein said molding spacer is made from synthetic resin and the orthodontic bracket is a lingual side orthodontic bracket for the teeth of upper and lower jaws.

12. An apparatus as claimed in claim 3, wherein said second means comprises a ring, and the orthodontic bracket further includes a hook integrated with the base member of the orthodontic bracket, so that said ring is inserted in said groove and hooked around the hook after the holding member has been inserted in said fitting recess, to thereby tightly assemble said suspension body and the orthodontic bracket together.

13. An apparatus as claimed in claim 12, wherein said ring is made from an elastic material.

14. An apparatus as claimed in claim 13, wherein said elastic ring is made from rubber.

15. An apparatus as claimed in claim 1, wherein said first means and said second means are integrally formed with each other.

16. An apparatus as claimed in claim 1, wherein said first means and said second means are separated from each other.

17. An apparatus for transferring an orthodontic bracket to a precisely predetermined position on a surface of a tooth, the orthodontic bracket including a base member having an adhesion surface to be adhered to the surface of the tooth, and a holding member and a hook respectively integrated with the base member, the holding member holding an orthodontic wire to be ligated by the orthodontic wire for correcting irregular set of teeth, said apparatus comprising:

a suspension body adapted to extend in parallel with the tooth from an apex toward a dental not of the tooth with a predetermined gap, said suspension body having an inner surface, at a lower end of which a filling recess is formed, and an outer surface, on a lower portion of which a groove is formed, said fitting recess having a contour complementary to a contour of the holding member for filled insertment of the holding member in said filling recess;

a ring inserted in said groove and hooked around the hook after the holding member has been inserted in said fitting recess, to thereby tightly assemble said suspension body and the orthodontic bracket together; and a molding spacer disposed between said suspension body and the tooth, which has first and second surfaces respectively facing the tooth and said suspension body, said first surface of said molding spacer having a contour complementary to a contour of the upper area of the tooth, said contour of said first surface of said molding spacer for fitted placement of said molding spacer on the upper area of the tooth, which includes an apex and upper portions of a labial surface and a lingual surface of the tooth, said second surface of said molding spacer having a contour complementary to a contour of said inner surface of said suspension body, said contour of said second surface of said molding spacer for fined engagement of said molding spacer with said suspension body.

\* \* \* \* \*

UNITED STATES PATENT AND TRADEMARK OFFICE
CERTIFICATE OF CORRECTION

PATENT NO. : 6,565,355 B2  
DATED : May 20, 2003  
INVENTOR(S) : Kim et al.

Page 1 of 1

It is certified that error appears in the above-identified patent and that said Letters Patent is hereby corrected as shown below:

Column 9,
Line 17, replace "not" with -- root --

Column 10,
Line 19, replace "fined" with -- fitted --

Signed and Sealed this

First Day of June, 2004

JON W. DUDAS
*Acting Director of the United States Patent and Trademark Office*